United States Patent [19]

Kourilsky et al.

[11] Patent Number: 4,581,333

[45] Date of Patent: Apr. 8, 1986

[54] METHOD OF DETECTING AND CHARACTERIZING A NUCLEIC ACID OR REACTANT FOR THE APPLICATION OF THIS METHOD

[75] Inventors: Philippe Kourilsky; Stratis Avrameas; Brigitte Cami nee Contamine; Jean-Luc Guesdon, all of Paris, France

[73] Assignee: Institut Pasteur, Paris, France

[21] Appl. No.: 373,017

[22] Filed: Apr. 29, 1982

Related U.S. Application Data

[63] Continuation of Ser. No. 169,370, Jul. 16, 1980, abandoned, which is a continuation of Ser. No. 29,375, Apr. 13, 1979, abandoned.

[30] Foreign Application Priority Data

Apr. 13, 1978 [FR] France ................................. 78 10975

[51] Int. Cl.$^4$ .......................... C12Q 1/68; C12Q 1/34; G01N 33/54; C12N 9/96
[52] U.S. Cl. ............................................ 435/6; 435/7; 435/188; 435/18; 435/810
[58] Field of Search ...................... 435/6, 7, 172, 188, 435/805, 810, 176, 177, 5, 18

[56] References Cited

U.S. PATENT DOCUMENTS

| | | | |
|---|---|---|---|
| 4,002,532 | 1/1977 | Weltman et al. | 435/188 |
| 4,067,774 | 1/1978 | Rubenstein et al. | 435/7 |
| 4,228,237 | 10/1980 | Hevey et al. | 435/188 |
| 4,318,980 | 3/1982 | Boguslaski et al. | 435/188 |

OTHER PUBLICATIONS

Manning et al., Biochemistry, 16(7):1364–1370 (1977).
Noyes et al., Cell, 5:301–310 (1975).
Reiser et al., Biochem. Biophys. Res. Comm., 85(3):1104–1112 (1978).
Wetmur, Biopolymers, 14:2517–2524 (1975).
Manning et al., Chromosoma (Berl.), 53:107–117 (1975).

*Primary Examiner*—Esther M. Kepplinger
*Attorney, Agent, or Firm*—Weiser & Stapler

[57] ABSTRACT

Method for detecting the possible presence of a DNA fragment, notably of a gene, in the midst of a complex sample of nucleic acids.

It comprises the hybridization of the sought fragment with a RNA probe, this being, prior or subsequent to the hybridization reaction, modified by an enzyme.

Application to seeking of particular genes or DNA fragments in the midst of a biological sample.

32 Claims, No Drawings

METHOD OF DETECTING AND CHARACTERIZING A NUCLEIC ACID OR REACTANT FOR THE APPLICATION OF THIS METHOD

This is a continuation of application Ser. No. 169,370, filed July 16, 1980 which in turn is a continuation of Ser. No. 029,375, filed Apr. 13, 1979, both now abandoned.

the invention relates to a method for detecting the presence and, if necessary, characterizing a nucleic acid or a sequence of the latter in a specimen which can contain it. It relates also to the reactants necessary for the application of this method. Finally it relates also to the application of such a method, among other possible applications, to the rapid in vitro diagnosis of the presence in a biological specimen, derived notably from a human or animal host, of particular nucleic particles, for example infectious in nature, or again the integrity or not of this or that particular gene belonging to the normal genetic patrimony of the host.

It is not necessary to dwell on the extraordinary richness in various nucleic acids which any biological specimen can contain, for example blood, which it is possible to sample from any living creature. It is also the same regarding different sequences, for example, of numerous genes which any particular nucleic acid may contain in this specimen; whence the immense difficulties that the genetician may encounter at the level of the detection or characterization of certain nucleic acids in a specimen, difficulties which also arise as soon as there is a question of characterizing the presence of certain fragments, for example of genes, contained in these nucleic acids.

The characterization of a particular nucleic acid or of particular genes—for example for the study of the organization of genetic sequences of DNA which contains them—hence involves the production previously from the medium studied, of a fraction enriched in this nucleic acid. To this end, there have already been proposed enrichment techniques exploiting hybridization reactions between the nucleic acid or the gene sought and a probe, to the extent that the latter was available and when the hybrids formed could then be separated from the medium, for example by differential sedimentation in a solution subjected to ultra-centrifugation.

Such probes have already been described: they are generally constituted by ribonucleic acids (RNA, DNA), such as the RNA obtained in the course of the genetic transcription of the structural genes contained in the desoxynucleic acids (DNA) of the cellular organisms from which they originate, these RNA being then capable of being themselves "translated" into proteins capable of being coded by these structural genes. It is known that these RNA have sequences of nucleotides complementary to those of the DNA from which they are derived, this complementarity being manifested by the capacity possessed by these RNA to form mixed hybrids with corresponding sequences of these DNA previously denatured, inasmuch as the latter were initially bi-catenary, for example after incubation in a high ionic strength medium and at a high temperature or in a basic medium.

It has been suggested to have recourse, for marking the hybrids formed, to radioactive labeling either of the genes themselves, or of the RNA probes. These techiques are however difficult to put into practice and, in addition, do not always enable satisfactory localization of the genes concerned in their DNA.

It is with the object of permitting easier localization of the genes under study in the DNA containing them, and of promoting a method of obtaining fractions enriched in predetermined segments of DNA from these same DNA that Hanning et al. proposed a physico-chemical detection technique for these genes, consisting of chemically modifying the RNA probe, by fixing biotin groups to the latter, through bridges formed by groups derived from cytochrome C and fixing physical marks visible with the scanning (electron) microscope, to the DNA, after hybridization with the probe, formed by submicroscopic spheres having diameters of about of 60 nm, notably based on poly(methacrylate), previously modified chemically and coupled in covalent manner to avidin molecules (notably in the articles entitled "A New Method of in situ Hybridization", *Chromosoma* (Berl.) 53. 107-117 (1975), Springer-Verlag 1975 and "A Method for Gene Enrichment Based on the Avidin-Biotin Interaction. Application to the *Drosophila* Ribosomal RNA Genes", *Biochemistry*, Vol. 16, No. 7, 1364-1369, 1977).

In fact, the incubation of hybrids modified with biotin in the presence of submicroscopic spheres modified with avidin permits the "labeling" and makes locatable the positions of the desired genes in the DNA which contains them, with respect to the overall structure also visible in the electronic microscope of this DNA, due to the fact of the very powerful non-covalent interactions which are then produced between the sites remaining free of the biotin and of the avidin.

This method however is hardly applicable to the purposes of rapid detection of the presence or absence of such genes and of such DNA in a biological specimen derived from a human or animal host, for example with the object of establishing rapid diagnosis either of the disease with which the host may possibly be afflicted, or of the integrity or not of a gene or of a DNA sequence, for example, in this host.

The invention arises from the conversion of the Manning et coll. method, which conversion leads to techniques of detection, even of characterization, capable of being applied in the absence of expensive equipment, by persons having only little laboratory experience.

The method of detection according to the invention of the possible presence or of the characterization of a sequence or particular fragment of nucleic acid, notably of a gene, even of the whole nucleic acid in a complex sample of nucleic acids, by contacting the sample, if necessary after prior denaturation of the nucleic acid under study, with a probe comprising a complementary nucleic acid, capable of being hybridized with the nucleic acid sequence of the nucleic acid sought, is characterized in that the reagent or probe used is a probe modified chemically by coupling or for its coupling with an enzyme prior or subsequent to the hybridization reaction, the possible presence of nucleic acid sequence or of the nucleic acid sought being revealable by the action of the thus-transformed product of the probe and of the sequence or of the nucleic acid sought, on an enzyme substrate.

Advantageously, the enzyme is selected according to its capacity to act on a chromogen substrate, which permits the measurement by optical or similar analysis, of the conversion ratio of the substrate, which ratio is then correlatable with the presence or not of the nucleic acid sequence or of the nucleic acid sought in the initial sample.

In a preferred embodiment of the application of the invention, the probe is modified by a chemical group capable of forming a stable complex with the enzyme or a molecule itself bound stably to the enzyme. Advantageously, the above-said chemical group and the above-said molecule are respectively constituted by biotin and avidin or vice versa, the enzyme being itself advantageously constituted by β-galactosidase.

It is self-evident that the chemical modification must be such that it does not prevent the possible subsequent hybridization of the probe with the DNA sequence or fragment sought.

It will immediately appear to the specialist that this technique permits a rapid determination of the presence or not in a biological sample of the gene or DNA fragment corresponding to the probe used, and this even in the presence of a considerable amount of other nucleic acids. This is particularly so due to the fact of the amplification at the level of detection which is obtained by the action of the enzyme fixed to the hybrid on the substrate brought into its presence. It is even possible, after sufficient purification of the hybrid, to obtain an indication as to the concentration in the DNA sought in the biological samples studied or as to the distribution ratio of the gene sought in a purified DNA, by measurement of the enzymatic activity observed.

Starting from a nucleic acid sample to be studied, it is possible to first carry out the hybridization, then the coupling reaction between the chemically modified and hybridized probe, on the one hand, of the enzyme, on the other hand, to then proceed with the separation or the degradation of the possible excess of non-hybridized probe and of the excess enzyme which has not reacted with the probe, before carrying out the above mentioned measurement.

As an alternative, the separation or degradation of the possible excess of non-hybridized probe may be carried out before the coupling reaction between the chemically modified and hybridized probe, on the one hand, and the enzyme, on the other hand.

The specific probe can be constituted by any specific RNA or DNA either single strand (mono-catenary), or denaturated previously by techniques known per se, if it relates to a DNA (or an RNA) initially double strand.

When the chemical modification of the probe is carried out by means of biotin, it is possible to resort to the technique described by Manning et coll. in the already mentioned publications, through cytochrome C, notably in the proportion of one molecule of biotin on the average for about 100 nucleotides.

Advantageously, recourse is then had for labeling the hybrid by the enzyme, to the product resulting from the coupling of avidin and the enzyme, notably β-galactosidase, by the Avrameas method ("Immunochemistry", 1969, 6, 43–52).

It goes without saying that it is possible to resort to other chemical modifications of the probe and, if necessary, of the enzyme, to effect their coupling, preferably after the hybridization reaction, and that it is possible to reverse the modifying agents of the probe and of the enzyme respectively.

Other pairs of modifying agents of the probe on the one hand, and of the enzyme, on the other hand, may also be used. By way of example, the following pairs are mentioned, the first of these agents being preferably used for the chemical modification of the probe and the second for the chemical modification of the enzyme. For example, the probe may be modified, by a known method, by metallic ions (mercury for example) and the development is done by means of an enzyme having hydrosulphide groups (—SH), or coupled to a support including such groups.

By way of example, which is of course non-limiting, of an experimental procedure which may be applied in the case where the sample to be analyzed is constituted by a blood specimen of some milliliters, it is possible to operate as follows:

The blood cells are first lysed and the DNA is extracted therefrom by a conventional technique.

A small amount of the DNA obtained, for example comprised between 1 and 100 μg, is denatured by 0.1 to 0.3N soda, the solution then being neutralized and brought back to pH 7.

To the solution obtained, the probe corresponding to the DNA fragment or to the DNA sought is then added in the proportion of about 1 μg of probe per 100 μg of denatured DNA (the amount of soda to be used is a function of the proportion of DNA sought in the specimen to be analyzed). The solution is then completed with salts for conferring on the medium a high ionic force, at least 0.3M NaCl, in the presence of 50% formamide and a chelating agent at low concentration, preferably in small volume. The hybridization can then be carried out at ordinary temperature for 1 to 40 hours (generally overnight). It is also possible to use the technique already described by Manning. As an alternative, any other hybridization technique can also be resorted to, for example, that described by KOHNE et al in "Biochemistry" (1977) (16, 5329–5341), at ordinary temperature in a phenol emulsion.

Avidin coupled to an enzyme such as β-galactosidase is then added to the medium under conditions permitting the coupling of the biotin of the probe with the free groups of the avidin of the coupling compound of the avidin and the enzyme.

The non-hybridized reagent is then separated from the hybridized reagent by conventional techniques, such as precipitation with polyethylene glycol, passage over gel, for example that of the type named SEPHAROSE, ultra-centrifugation, etc.

As an alternative it is also possible to carry out the separation of the non-hybridized probe before the coupling of the avidin bearing the enzyme with the biotin groups coupled to the hybridized probe with the DNA.

The enzyme possibly fixed and consequently the possible effective hybridization of the probe with the DNA studied may be visualized or detected by placing in contact with the medium a substrate of the enzyme, notably that constituted by orthonitrophenol galactoside (ONPG).

It is self-evident that the experimental conditions once well-fixed, it is possible to determine a measurable activity threshold, for example, by a colorimetric or fluorographic technique, beyond which it is possible to conclude in the presence in the treated sample of DNA or of the DNA fragments sought.

The following description of a test carried out in the laboratory has simply the purpose of illustrating the manner in which the process according to the invention may be put into practice, it being obviously understood that the modifications at the level of techniques, according to the nature of the biological specimen studied and of that of the DNA or of the DNA fragment sought, are within the evident scope of the technician skilled in the art.

Experiments were carried out on the model consisting of detecting the presence of a mouse DNA by hybridization of this DNA with a mouse ribosomic RNA used as a probe.

Mouse DNA (100 µg per 100 µl of aqueous solution) is denatured by addition of soda (10 µl of 1M NaOH). 10 minutes later, the solution was brought back to pH neutral by the addition of 10µl of 1.5M acid sodium phosphate $NaH_2PO_4$.

1 µg of ribosomic RNA labeled with biotin by means of cytochrome C, prepared by the technique of Wanning & Coll., is added to the denatured DNA solution. The volume was adjusted to 160 µl with water. 40 µl of a solution having a concentration of mineral salts equal to twenty times that of the solution called SSC (abbreviation of the English expression "standard saline citrate") and 200 µl of redistilled or deionized formamide was then added to the medium. It is recalled that the SSC solution is an aqueous solution of 0.15M sodium choloride, 0.015M sodium citrate, at pH 7.0.

The mixture was incubated until the next day at ordinary temperature, then dialyzed at 4° C. against a solution having a double concentration of the SSC solution, then for 8 hours against 500 ml of a phosphate buffer at pH 7.0 containing phosphate at a concentration of 0.1M, sodium chloride at a concentration of 1M and ethylene-diamine-tetrasodium acetate (EDTA) at a concentration of 0.01M. The latter dialysis is then repeated twice, each time for 8 hours.

The solution thus-obtained was treated with pancreatic ribonuclease for 1 hour at ordinary temperature, to obtain a final concentration of 10 µg per ml of ribonuclease, this treatment permitting the degradation of the non-hybridized RNA.

To the medium obtained was then added a solution of cytochrome C (1 mg per ml) and 1 microliter of a solution containing 1 mg per ml of avidin and 2 mg per ml of β-galactosidase, of which 1 molecule of β-galactosidase in seven is coupled with avidin. It is mixed and the solution is then left to stand at 4° C. for 4 hours. The medium was then diluted to 10 ml with the phosphate dialysis buffer and the solution obtained is subjected to ultracentrifugation for 1 hour at 35,000 rpm (in a BECKMAN ROTOR SW 41 centrifuge). The DNA and the hybridized RNA are to be found in the centriguation culot, as well as the avidin β-galactosidase bound to this RNA. The supernatant liquor contains the non-hybridized RNA degraded by the ribonuclease and the unbound avidin β-galactosidase.

The culot is collected and resuspended in 10 ml of buffer. It is recentrifuged and the culot is taken up again in 0.5 ml of buffer (tube No. 1) and the activity of the β-galactosidase on the ONPG substrate is assayed by the technique described by Miller ("Experiments in bacterial genetics, 1972, Cold Spring Harbor Laboratory", Cold Spring Harbor, N.Y. U.S.A.), by measurement of the eptical density of the medium at 420 mµ, after incubation of the medium at 37° C. for 30 minutes or more.

Controls are prepared under conditions strictly identical with those which have been described above, except that in a first case the initial addition of ribosomic RNA (tube No. 2) was omitted and in the other case the addition of mouse DNA (tube No. 3) was omitted.

The results of the three assays carried out are shown in the table below:

| Tube No, | Contents | | Results of the assay (optical density at 420 mu after 30 minutes at 37° C. |
|---|---|---|---|
| | DNA | RNA | |
| 1 | + | + | 0.45 |
| 2 | + | − | 0.14 |
| 3 | − | + | 0.15 |

The signs + and −, respectively in the columns under the headings DNA and RNA, signify the presence or absence either of DNA, or of RNA, in the initial medium.

As can be observed on examining this table, the optical density measured in tube No. 1 (containing the hybrid) is very significantly greater than the optical densities measured in the control tubes.

The experimental model which has just been described therefore illustrates the conditions under which the possible presence of a desired DNA or DNA fragment may be detected, to the extent that a probe complementary to this DNA or to this RNA fragment is available by resorting to a simple technique requiring neither very complicated laboratory equipment nor a particularly experienced technician.

The invention is applicable particularly advantageously to in vitro diagnosis operations of the presence, for example in a biological sample (blood sample, specimen of stools, etc.) of various viruses, such as those named Herpes, Epstein Barr, virus Pox, cytomegalo, etc. In the same way, the invention may be applied to the diagnosis, for example, of specific chromosomic anomalies.

It is also applicable to the realization of bacterial diagnoses, in particular in the case where individuals are bearers of pathogenic genes, both expressed and non-expressed (or latent).

It will appear naturally to the specialist, in the case of investigating an infectious DNA, that it is possible to conclude rapidly as to the healthy character of the treated biological specimen, and having regard to the nucleic acid or the fragment of nucleic acid sought, in the absence of induction observe on the chromogenic substrate, or at least an over-shoot of the activity threshold, either predetermined experimentally, or by comparison with controls free of the virus.

Conversely, the absence of action observed with respect to the chromogenic substrate, notably beyond the above-mentioned threshold, can, in the other type of application, envisaged above by way of example, translate the presence of an anomaly of the chromosomic anomaly sought, in the absence of observed total or partial hybridization, between the probe and the DNA studied.

It is advantageously possible to place, for example, at the disposal of medical analysis laboratories, "kits" containing all of the essential reactants for the application of the process according to the invention. These kits can, in particular, contain a sampling of probes corresponding, for example, to the DNA of the virus or bacteria, of conventionally sought pathogenic viruses or bacteria, or even of probes relating to particular genes which should normally be contained in biological specimens, notably blood specimens, under test.

In this regard, the invention relates hence to a "kit" characterized in that it comprises:
 at least one specific probe formed from RNA or a single RNA strand, characteristic of a nucleic acid sequence or of a nucleic acid to be sought, this probe being modified chemically for its coupling with an enzyme, said enzyme, if necessary, modified so as to be able to be coupled with said probe, a substrate, notably a chromogene, specific to the enzyme, the reactants necessary for the lysis of the cellular medium to be studied, notably a blood medium, and for the extraction of nucleic acids from the cells of this medium.

As has already been observed in the foregoing, it is advantageous to constitute the modified probe by a probe to which biotin is bound, the modified enzyme being then constituted by the enzyme itself, for example β-galactosidase, coupled to avidin.

The invention relates also moreover, by way of novel industrial product, to the coupling product of an enzyme (of which the action may be revealed with respect to a substrate, notably chromogenic) and of a probe (RNA or single strand DNA), either directly, or through a coupling agent. It relates also again to the coupling product of the enzyme and of at least one chemical molecule, the whole then being capable of being coupled in its turn with a probe (RNA or DNA), if necessary modified, itself capable of being hybridized with a DNA or a DNA fragment. By way of examples of such novel industrial products, may be mentioned the coupling products of a probe (RNA or DNA) with an enzyme, such as β-galactosidase, or again coupling products of avidin or of biotin with such an enzyme.

Of course, the invention may be applied in other fields of application, notably for the labeling of certain DNA fragments in well-known genetic experiments seeking to establish the genotype of the DNA concerned. In particular, the invention may be applied to the determination of the incorporation or not of a particular DNA fragment in experiments of genetic sorting comprising for example operations of transforming DNA from an infected cell with a foreign DNA containing the DNA fragment concerned or on the contrary operations of transduction including the incorporation of a DNA fragment concerned, normally contained in the DNA of the cell, in the DNA of the virus used for the infection of the cell, etc., to the extent that, of course, a probe constituted by the RNA fragment or DNA complementary to the sought nucleic acid fragment is available.

As is self-evident and as emerges already besides from the foregoing, the invention is in no way limited to those of its modes of application and embodiments which have been more especially envisaged; it encompasses on the contrary all modifications, notably those where recourse is had to modifications of the probe which may enable the enzymatic assay of the hybrid and modifications relating to the formation and/or purification of the hybrids, to the labeling or the chemical modification of the DNA studied itself, under conditions which have been described above, the RNA probe not being the subject of any particular labeling; such an inversion of the reactants may be envisaged, for example in the case of a DNA including numerous examples of repetetive genes, that it is desired to isolate from the whole DNA, in the form of a hybrid with a probe, after fragmentation of the DNA concerned by conventional techniques. It is self-evident that these equivalents are included within the field of protection defined by the claims.

By way of yet another modification, it is possible to have recourse to a process consisting of marking the hybrid formed by the desired DNA and the probe, by means of an anti-hybrid antibody, coupled to an enzyme such as β-galactosidase.

We claim:

1. A detection method for detecting the presence or absence of a nucleic acid in a biological medium, the medium containing also other nucleic acids which are not sought to be detected, by means of a probe containing a nucleic acid complementary of said nucleic acid sought to be detected and by means of measurement on a substrate specific to an enzyme, which method comprises:

hybridizing the nucleic acid sought to be detected with said probe having a complementary nucleic acid, thereby forming a hybridized product, separating excess non-hybridized probe from said hybridized product and the other nucleic acids, coupling the hybridized product with an enzyme, thereby forming an enzyme-bonded product, wherein either said probe is modified by a chemical group for coupling with the enzyme of said enzyme is modified by a chemical group for coupling with said probe, measuring the activity of the enzyme-bonded product on the subtrate specific to the enzyme in the presence of the other nucleic acids, thereby detecting whether or not the nucleic acid is present.

2. The method of claim 1 wherein the chemical modification is performed prior to hybridization.

3. The method of claim 1 wherein the hybridized product is coupled directly to the enzyme.

4. The method of claim 3 wherein the enzyme is modified by avidin.

5. The method of claim 1 wherein the probe is chemically modified.

6. The method of claim 5 wherein to the hybrid there is affixed an anti-hybrid antibody, thereby forming a complex.

7. The method of claim 6 wherein to the complex there is coupled an enzyme.

8. The method of claim 5 wherein the probe is modified by biotin or avidin.

9. The method of claim 8 wherein the probe is modified by biotin through the intermediary of cytochrome C.

10. The method of claim 1 wherein the enzyme has an —SH group.

11. The method of claim 1 wherein the enzyme is beta-galactosidase.

12. The method of claim 11 wherein the substrate for the enzyme is orthonitrophenol galactoside.

13. The method of claim 1 wherein the complementary nucleic acid is selected from the group consisting of DNA and RNA.

14. The method of claim 13 wherein the DNA or RNA is single-stranded.

15. The method of claim 1 wherein the step of separating the non-hybridized nucleic acid is separated after the bonding but prior to the measuring step.

16. A detection method for detecting the presence or absence of a nucleic acid in a biological medium, the medium containing also other nucleic acids which are not sought to be detected, by means of measurement on a substrate specific to a chemically-modified enzyme, which comprises:

hybridizing the nucleic acid sought to be detected with a probe having a complementary nucleic acid, thereby forming a hybridized product, separating excess non-hybridized probe from said hybridized product and the other nucleic acids, coupling the hybridized product with an enzyme which is chemically-modified to bind to the probe of the hybridized product, thereby forming a chemically modified enzyme-coupled product, measuring the activity of the chemically-modified enzyme-coupled product on the substrate specific to the enzyme in the presence of the other nucleic acids, thereby detecting whether or not the nucleic acid is present.

17. The method of claim 16 wherein the probe is a chemically-modified probe.

18. A composition of matter for detecting the presence or absence of a nucleic acid in a biological sample containing said nucleic acid and other nucleic acids, the presence or absence of which is not sought to be detected, said composition of matter comprising an enzyme, a probe modified by a chemical group for coupling with said enzyme and comprising a complementary nucleic acid sequence which is hybridizable with the nucleic acid sought to be detected to thereby form a hybridized product-enzyme complex, and a substrate specific to the enzyme, for the detection of said hybridized product-enzyme complex.

19. The composition of matter of claim 18 wherein the substrate is a chromogen.

20. The composition of matter of claim 18 wherein the chemical group is selected from the group consisting of biotin and avidin.

21. The composition of matter of claim 20 wherein the probe is modified with biotin and the enzyme with avidin.

22. A composition of matter which comprises a biological sample containing a nucleic acid sought to be detected and other nucleic acids, a probe which comprises a nucleic acid sequence complementary to the nucleic acid sought to be detected and hybridized therewith, which composition is substantially free of unhybridized probe and in which composition the hybridized probe is modified by a chemical group and said probe is bonded to an enzyme through said chemical group and which composition of matter is capable of acting on a substrate specific to the enzyme.

23. The composition of matter of claim 22 wherein the chemical group is selected from the group consisting of biotin and avidin.

24. The composition of matter of claim 22 wherein the hybridized probe is bonded directly to the enzyme.

25. An article of manufacture for detecting the presence or absence of a nucleic acid in a biological sample containing other nucleic acids the presence or absence of which is not sought to be detected, which article comprises a probe which comprises a complementary nucleic acid sequence which is hybridizable with the nucleic acid sought to be detected, an enzyme and a substrate specific for the enzyme, and wherein either said probe is modified by a chemical group for coupling with the enzyme or said enzyme is modified by a chemical group for coupling with said probe.

26. The article of claim 25 wherein the enzyme is modified by a chemical group.

27. The article of claim 25 which comprises a reactant for the lysis of the biological sample.

28. The article of claim 25 wherein the chemical is selected from the group consisting of biotin and avidin.

29. The article of claim 25 wherein the probe is coupled to biotin and the enzyme to avidin.

30. The article of claim 29 wherein the enzyme is beta-galactosidase.

31. The article of claim 25 wherein the chemical is selected from the group consisting of biotin and avidin, the enzyme is beta-galactosidase and the substrate is orthonitrophenol galactoside.

32. The article of manufacture of claim 25 further comprising the nucleic acid to be detected in an amount sufficient for detection.

* * * * *